US006506726B1

(12) United States Patent
Dobbins et al.

(10) Patent No.: US 6,506,726 B1
(45) Date of Patent: Jan. 14, 2003

(54) PURIFICATION OF ECHINOCANDIN CYCLOPEPTIDE COMPOUNDS

(75) Inventors: John Robert Dobbins, Indianapolis, IN (US); Eugene Paul Kroeff, Carmel, IN (US); Jeffrey Thomas Vicenzi, Brownsburg, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 09/857,924

(22) PCT Filed: Dec. 8, 1999

(86) PCT No.: PCT/US99/29008

§ 371 (c)(1),
(2), (4) Date: Dec. 10, 2001

(87) PCT Pub. No.: WO00/34315

PCT Pub. Date: Jun. 15, 2000

Related U.S. Application Data

(60) Provisional application No. 60/111,524, filed on Dec. 8, 1998.

(51) Int. Cl.[7] ............................ A61K 38/00; C07K 1/14
(52) U.S. Cl. ........................... 514/11; 514/11; 514/9; 514/2; 530/317; 530/344; 530/345
(58) Field of Search ................... 514/9, 11, 2; 530/317, 530/344, 345

(56) References Cited

U.S. PATENT DOCUMENTS

| | | | |
|---|---|---|---|
| 4,293,482 A | 10/1981 | Abbott et al. | 260/112.5 R |
| 4,293,489 A | 10/1981 | Debono | 260/112.5 R |
| 4,304,716 A | 12/1981 | Abbott et al. | 260/112.5 R |
| 4,320,052 A | 3/1982 | Abbott et al. | 260/112.5 R |
| 4,874,843 A | 10/1989 | Baker | 530/317 |
| 5,166,135 A | 11/1992 | Schmatz | 514/11 |
| 5,541,160 A | 7/1996 | Balkovec et al. | 514/11 |
| 5,696,084 A | 12/1997 | Lartey et al. | 514/9 |
| 5,932,543 A | 8/1999 | Burkhart et al. | 514/11 |
| 5,965,525 A | 10/1999 | Burkhart et al. | 514/11 |

FOREIGN PATENT DOCUMENTS

| | | |
|---|---|---|
| EP | 0 294 990 A2 | 12/1988 |
| EP | 0 359 529 A1 | 3/1990 |
| EP | 0 448 353 A2 | 9/1991 |
| EP | 0 462 531 A2 B1 | 12/1991 |
| EP | 0 460 882 A2 A3 B1 | 12/1991 |
| EP | 0 561 639 A1 | 9/1993 |
| EP | 0 931 834 A2 | 7/1999 |
| WO | WO 96/31228 | 10/1996 |
| WO | WO 96/37509 | 11/1996 |
| WO | WO 96/37510 | 11/1996 |
| WO | WO 96/37511 | 11/1996 |
| WO | WO 96/37512 | 11/1996 |
| WO | WO 97/05163 | 2/1997 |
| WO | WO 97/27864 | 8/1997 |
| WO | WO 99/06062 | 2/1999 |
| WO | WO 99/43337 | 9/1999 |
| WO | WO 00/12540 | 3/2000 |
| WO | WO 00/11023 A2 A3 | 3/2000 |
| WO | WO 00/24694 | 5/2000 |
| WO | WO 00/35944 | 6/2000 |
| WO | WO 00/35945 | 6/2000 |
| WO | WO 00/51564 | 9/2000 |
| WO | WO 00/51567 | 9/2000 |
| WO | WO 00/52036 | 9/2000 |
| WO | WO 00/52037 | 9/2000 |

OTHER PUBLICATIONS

U. S. patent application Ser. No. 07/992,390, Burkhardt et al., filed Dec. 16, 1992.
U. S. patent application Ser. No. 08/032,228, Burkhardt et al., filed Mar. 17, 1993.
Boeck, L. D. et al. (1989). "Deacylation of Echinocandin B by Actinoplanes Utahensio", *The Journal of Antibiotics*, XLII(3):382–388.
Evans, D. A. et al. (1987). "Synthesis of the Cyclic Hexapeptide Echinocandin D. New Approaches to the Asymmetric Synthesis of β–Hydroxy α–Amino Acids", *J. Am. Chem. Soc.* 109:7151–7157.
Grieser, M. D. (1973). "Liquid Chromatography on a Porous Polystyrene–Divinylbenzene Support; Separation of Nitro– and Chlorophenols", *Analytical Chemistry* 45:1348–1353.
Kurokawa, N. et al. (1986). "Total Synthesis of Echinocandins. 1. Stereocontrolled Syntheses of Constituents Amino Acids", *J. Am. Chem. Soc.* 108:6041–6043.
Kurokawa, N. et al.(1993). "Synthesis Studies on Antifugal Cyclic Peptides, Echinocandins. Stereoselective Total Synthesis of Echinocandin D via a Novel Peptide Coupling", *Tetrahedron*, 49:6195–6222.
Voser, W. et al. (1980). "Influence of Cations and Anions on the Separation Properties of Macroporous Polystyrene–Type Resins for Cephalosporins", *Journal of Chromatography* 201:287–292.
Ziambias, R. et al. (1992). "Preparation and Stucture—Activity Relationship of Simplified Analogues of the Antifungal Agent Cilofungin: A Total Synthesis Approach.", *J. Med. Chem.* 35:2843–2855.

*Primary Examiner*—Gabrielle Bugaisky
*Assistant Examiner*—Chih-Min Kam
(74) *Attorney, Agent, or Firm*—Morrison & Foerster LLP

(57) ABSTRACT

A method is described for separating and purifying a wide variety of fermentation cyclopeptide products containing at least one protonatable amino group (including the deacylated Echinocandin-type compounds) from their fermentation or mixed broths and partially purified process streams by adsorbing the mixture onto a hydrophobic, reversed phase chromatographic media and eluting with a continuous linear acetic acid gradient ranging from 0.1% acetic acid to 10.0% acetic acid by volume in water. A process for removing tripeptide-aldehyde by-products from the fermentation products by means of a derivatizing agent is also described.

19 Claims, No Drawings

PURIFICATION OF ECHINOCANDIN CYCLOPEPTIDE COMPOUNDS

CROSS REFERENCE TO RELATED APPLICATIONS

This is a U.S. National Phase of International Application PCT/US99/29008, filed on Dec. 8, 1999, which claims priority to U.S. Provisional Patent Application Ser. No. 60/111,524, filed Dec. 8, 1998, the disclosures of which are incorporated herein by reference in their entirety.

TECHNICAL FIELD

The present invention relates to a process for purification of cyclopeptide compounds containing at least one protonatable amino group, in particular, the process relates to the purification of an Echinocandin-type compound by adsorption onto a hydrophobic, reversed phase chromatographic media and eluting with a continuous nearly linear gradient of increasing acetic acid. A purification process is also provided for selectively removing a tripeptide-aldehyde by-product of the Echinocandin fermentation process to yield a higher purity Echinocandin compound.

BACKGROUND ART

Echinocandin cyclopeptides are natural products that have been shown to have antifungal activities. Included in the Echinocandin cyclopeptide family are natural products such as Echinocandin B (ECB), Echinocandin C, Aculeacin A$\gamma$y, Mulundocandin, Sporiofungin A, Pneumocandin A$_0$, WF11899A, and Pneumocandin B$_0$. The natural products are typically produced by culturing various microorganisms. For example, Echinocandin B is produced from the fermentation of the fungus, *Aspergillus nidulans*.

In the search for more active materials, the natural products have been modified in a variety of ways. One of the most common modifications has been the replacement of the N-acyl side chain on the natural product to produce a semi-synthetic derivative. For example, U.S. Pat. Nos. 4,293,489; 4,320,052; 5,166,135; and 5,541,160; and EP 359529; 448353; 447186; 462531; and 561639 describe a variety of N-acyl derivatized Echinocandin compounds that provide varying degrees of antifungal activity.

The N-acyl derivatives are produced by deacylating the natural product followed by reacylation with a different acyl group. The deacylation is typically achieved by means of an enzyme (e.g., deacylase enzyme). The deacylase enzyme may be obtained from the microorganism *Actinoplanes utahensis* or Pseudomonas species. See i.e., U.S. Pat. Nos. 4,293,482; and 4,304,716; and EP 460,882. The deacylated compound is typically referred to as the nucleus of the corresponding natural product (i.e., the deacylated product of Echinocandin B is referred to as the Echinocandin B nucleus (ECBN)). Unfortunately, both the fermentation and deacylation processes produce several by-products that are difficult to remove and decrease the purity of the desired deacylated cyclic peptide nucleus.

U.S. Pat. No. 4,874,843 describes a chromatographic process using non-functional resins in a reversed mode to purify Echinocandin-type products. Even though the process improved the purity of products derived from a fermentation process, further improvements are still needed to remove contaminants that are difficult to separate from both the intermediate deacylated nucleus and the final acylated pharmaceutically active compounds. Since the potency of the final pharmaceutical product is dependent upon the purity of the intermediates used to make the final product, improvements in purity at any stage of the manufacturing process are highly desirable. Ideally, the contaminants are removed at the earliest stage possible in the manufacturing process.

General discussions of non-functional resins and their applications in liquid chromatographic separations may be found in *J. Chromatography*, 201, 287–292 (1980) and Grieser, M.D. et al, *Analytical Chemistry*, 45, 1348–1353 (1973). The use of either step or continuous gradients are discussed; however, the eluents contain significant amounts of organic solvents. In a manufacturing process, the use of organic solvents raises several concerns such as environmental regulations (e.g., air quality emission standards), special handling requirements (e.g., flammability standards) and disposal limitations (e.g., toxic waste regulations). Therefore, there is a need for an eluent system that minimizes the use of organic solvents yet effectively separates mixtures into their pure components.

DISCLOSURE OF THE INVENTION

The present invention provides a method for separating and purifying a wide variety of fermentation cyclopeptide products containing at least one protonatable amino group (including the deacylated Echinocandin-type compounds) from their fermentation or mixed broths and partially purified process streams by adsorbing the mixture onto a hydrophobic, reversed phase, chromatographic media and eluting with a continuous nearly linear acetic acid gradient ranging from 0.1% acetic acid to 10.0% acetic acid by volume in water, preferably from 0.5% (pH=5.5) to 4.0% (pH=2.5) acetic acid.

In another embodiment of the present invention, a process for purifying Echinocandin-type compounds (including simple derivatives thereof) is provided where an aldehyde by-product (in particular, a tripeptide-aldehyde by-product) in the fermentation mixture or partially purified mixture is reacted with a derivatizing agent. Preferably, the fermentation broth or mixed broth is reacted with the derivatizing agent prior to purification of the corresponding Echinocandin nucleus using the method described above.

As used herein, the term "derivatizing agent" refers to a reagent capable of reacting with the aldehyde functionality of the tripeptide by-product to produce an intermediate that is sufficiently different in hydrophobicity to allow separation of the tripeptide intermediate from the desired Echinocandin-type compound.

The term "protonatable amino group" refers to an amino group that undergoes protonation when subjected to the eluting conditions of the present invention (i.e., 0.1% acetic acid to 10% acetic acid by volume in water).

The term "Echinocandin-type compounds" refers to compounds having the following general structure including any simple derivatives thereof:

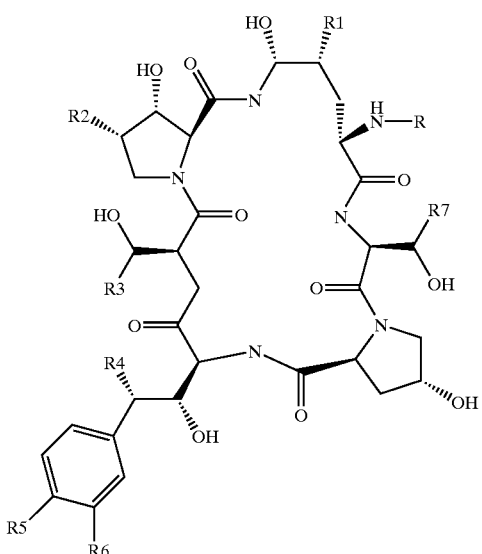

wherein R is a hydrogen or —C(O)R' where R' is an alkyl group, an alkenyl group, an alkynyl group, an aryl group, or heteroaryl group having attached thereon at least one protonatable amino group; R1 is —H or —OH; R2 is —H or —CH$_3$; R3 is —H, —CH$_3$, —CH$_2$CONH$_2$ or —CH$_2$CH$_2$NH$_2$; R4 is —H or —OH; R5 is —OH, —OPO$_3$H$_2$, or —OSO$_3$H; and R6 is —H or —OSO$_3$H. "Echinocandin nucleus" refers to the deacylated Echinocandin compound where R is a hydrogen. "ECBN" refers to the Echinocandin B nucleus where R1, R4 and R5 are hydroxyl groups, R2, R3, and R7 are methyl groups; and R1 and R6 are hydrogens.

The term "alkyl" refers to a hydrocarbon radical of the general formula C$_n$H$_{2n+1}$ containing from 1 to 30 carbon atoms unless otherwise indicated. The alkane radical may be straight (e.g. methyl, ethyl, propyl, butyl, etc.), branched (e.g., isopropyl, isobutyl, tertiary butyl, neopentyl, etc.), cyclic (e.g., cyclopropyl, cyclobutyl, cyclopentyl, methylcyclopentyl, cyclohexyl, etc.), or multi-cyclic (e.g., bicyclo[2.2.1]heptane, spiro[2.2]pentane, etc.). The alkane radical may be substituted or unsubstituted. Similarly, the alkyl portion of an alkoxy group or alkanoate has the same definition as above.

The term "alkenyl" refers to an acyclic hydrocarbon containing at least one carbon-carbon double bond. The alkene radical may be straight, branched, cyclic, or multi-cyclic. The alkene radical may be substituted or unsubstituted.

The term "alkynyl" refers to an acyclic hydrocarbon containing at least one carbon-carbon triple bond. The alkene radical may be straight, or branched. The alkyne radical may be substituted or unsubstituted.

The term "aryl" refers to aromatic moieties having single (e.g., phenyl) or fused ring systems (e.g., naphthalene, anthracene, phenanthrene, etc.). The aryl groups may be substituted or unsubstituted.

The term "heteroaryl" refers to aromatic moieties containing at least one heteroatom within the aromatic ring system (e.g., pyrrole, pyridine, indole, thiophene, furan, benzofuran, imidazole, pyrimidine, purine, benzimidazole, quinoline, etc.). The aromatic moiety may consist of a single or fused ring system. The heteroaryl groups may be substituted or unsubstituted.

Within the field of organic chemistry and particularly within the field of organic biochemistry, it is widely understood that significant substitution of compounds is tolerated or even useful. In the present invention, for example, the term alkyl group allows for substitutents which is a classic alkyl, such as methyl, ethyl, propyl, hexyl, isooctyl, dodecyl, stearyl, etc. The term "group" specifically envisions and allows for substitutions on alkyls which are common in the art, such as hydroxy, halogen, alkoxy, carbonyl, keto, ester, carbamato, etc., as well as including the unsubstituted alkyl moiety. However, it is generally understood by those skilled in the art that the substituents should be selected so as to not adversely affect the pharmacological characteristics of the compound or adversely interfere with the use of the medicament. Suitable substituents for any of the groups defined above include alkyl, alkenyl, alkynyl, aryl, halo, hydroxy, alkoxy, aryloxy, mercapto, alkylthio, arylthio, mono- and di-alkyl amino, quaternary ammonium salts, aminoalkoxy, hydroxyalkylamino, aminoalkylthio, carbamyl, carbonyl, carboxy, glycolyl, glycyl, hydrazino, guanyl, and combinations thereof.

BEST MODE FOR CARRYING OUT THE INVENTION

Fermentation and mixed broths contain a number of by-products that are very difficult to separate from the desired cyclopeptide product. "Mixed broth" refers to a conversion mixture where the fermentation broth is treated directly with a deacylating enzyme without purification to produce the deacylated product (e.g. ECBN). Reversed-phase, liquid chromatography has been used in the past with reasonable success; however, the need for higher purity compounds demands more improved methods of purification. Applicants have discovered that the separation of fermentation by-products from the desired fermentation product containing a protonatable amino group can be improved by using a reversed-phase chromatographic media in combination with a continuous, nearly linear acetic acid elution scheme.

Suitable hydrophobic chromatographic media include reversed phase silicas, and organic polymers such as copolymers of styrene and divinylbenzene, methacrylate polymer. A variety of reversed-phase silicas are commercially available from vendors such as BTR, E. Merck, Eka Nobel, Millipore, Phenomenex, Whatman, or YMC. The silicas are derivatized with straight chain alkyl hydrocarbons ranging in length from C$_1$ to C$_{18}$ (C$_1$, C$_4$, C$_8$ and C$_{18}$ being the most common) or other hydrophobic ligands such (e.g. phenyl or cyano). A variety of styrene/divinylbenzene resins designed for reversed-phase, liquid chromatography are also available commercially such as Diaion™ HP and SP resins (available from Mitsubishi Chemical Industries Limited, Tokyo, Japan), and Amberlite XAD-2,4, and 16 resins (available from Rohm and Haas Chemical Co., Philadelphia, Pa.), and the CG-161, 300, and 1000 Amberchrom resins from Toso Haas (Montgomeryville, Pa.). Non-functional resins are generally characterized by their pore volume (0.5–4.5 ml/g), specific surface area (200–800 m$^2$/g), pore diameter (40–1300 Å), pore size distribution and/or bead size distribution. Preferred non-functional resins include Diaion HP-20 having a surface area of 500 m$^2$/g, a pore size of 200–300 Å and particle size of 200–800 μm; SP-825 having a surface area of 1,000 m$^2$/g, pore size of 50–60 Å and particle size of 250–600 μm; SP-207 (brominated version of HP-20) having a surface area of 630 m$^2$/g, pore size of 100–200 Å and particle size of 200–800 μm; and CG-161CD having a surface area of 900 m$^2$/g, pore size of 110–175 Å, and particle size of 80–160 μm. More preferred are the HP-20 and SP-825 resins.

Initially, a crude or partially purified solution is provided that contains the desired cyclic peptide compound having at least one protonatable amino group. Generally, the amino group can be protonated during the course of the acetic acid gradient that spans the pH range from 5.5 to 2.5. Preferably the amino group is a primary amine; however, the amino group may be a secondary amine or tertiary amine so long as the additional substituents on the nitrogen atom are not sufficiently hydrophobic such that they overcome the polarity of the positively charged amine. The solution may originate from a fermentation process or a synthetic process. For example, the cyclic peptide compounds may be prepared by the synthetic methods described in U.S. Pat. No. 5,696, 084; *J. Am. Chem. Soc.*, 108, 6041 (1986); Evans, D. A., et al., *J. Am. Chem. Soc.*, 109, 5151 (1987); *J. Med. Chem.*, 35, 2843 (1992); and Kurokawa, N., et al., *Tetrahedron*, 49, 6195 (1993). The crude solution is usually a mixed broth. Alternatively, the process may be used to further purify (or polish) partially purified material.

Depending upon the particular fermentation process used, it may be desirable to prefilter the solution to remove particulates that may interfere with the chromatographic process. Filtration may be accomplished by any number of means known to those skilled in the art including gravity filtration, vacuum filtration through a ceramic filter which may or may not include a Celite™ filter aid, etc. Solids in the fermentation broth may also be removed by centrifugation followed by decanting the liquid from the solids.

The fermentation solution may be concentrated if desired using a variety of means which are also well known to those skilled in the art such as evaporative concentration, lyophilization, etc. The concentrate may be filtered a second time to remove any precipitate that may have formed during the concentration process.

The crude or partially purified solution is loaded onto a chromatography column packed with one of the hydrophobic chromatographic media described above. The desired cyclic peptide product is then eluted from the chromatographic media using a continuous nearly linear gradient ranging from about 0.1% acetic acid to about 10% acetic acid, preferably from about 0.5% acetic acid (pH=5.5) to about 4% acetic acid (pH=2.5). The upper end of the range of acetic acid concentration selected is based upon the stability of the chromatographic media used and the stability of the compound being purified at that pH. The lower end of the range is selected based upon the pH where the amino group is protonated and concentration of acetic acid required to elute the product from the hydrophobic surface. Those skilled in the art will appreciate that the gradient does not have to be perfectly linear. Within the meaning of "nearly linear" includes a flat convex or concave gradient.

At the end of the gradient elution process step, an additional volume of the higher concentrated acetic solution is typically used to complete the elution. At the end of the process, the column may be regenerated so that the column may be re-used for additional purification cycles. The regeneration step typically involves washing the column with mixtures of an organic solvent and water at both a neutral and alkaline pH to remove any residual materials left on the column matrix. Suitable solvents include acetonitrile, methanol, isopropanol, and acetone. The linear acetic acid elution scheme not only provides good selectivity (see i.e., Example 1 below), but also limits the use of organic solvents to the regeneration step of the column operation. Thus, both the absolute quantity of organic solvent used and the volume of column effluent that must be treated prior to disposal is minimized.

The fermentation product may be recovered from the eluate using a variety of methods. Suitable recovery methods include crystallization, evaporative concentration, and lyophilization.

The fermentation broth for Echinocandin B contains varying levels of a tripeptide-aldehyde (Asn-Gln-Leu-H) by-product having the following chemical structure (Ia). The tripeptide-aldehyde by-product under goes deacylation as well as Echinocandin B during the enzymatic deacylation process to form the corresponding deacylated tripeptide-aldehyde (Ib).

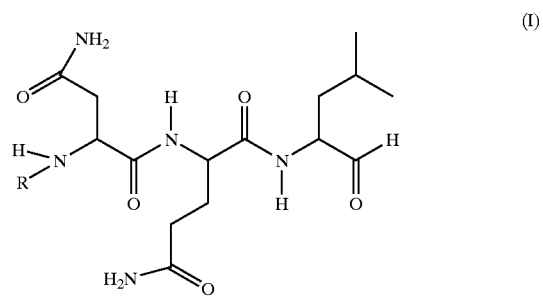

(I)

where R is $C(O)CH_2CH(OH)C_9H_{19}$ (Ia—fermentation by-product) or a hydrogen (Ib—deacylation by-product from a mixed broth).

Surprisingly, the retention time of the deacylated tripeptide-aldehyde is very similar to ECBN in reversed phase, liquid chromatography, even under optimum elution conditions, thus making it very difficult to separate the deacylated tripeptide-aldehyde (Ib) from the desired ECBN. If the tripeptide is not removed, then the free amino group of the tripeptide competes with the free amino group of the ECBN compound during the reacylation process. As a result, an excess of acylating compound must be added to insure complete acylation of the ECBN compound. The tripeptide contaminate not only consumes needed starting materials but also produces an acylated by-product that is difficult to remove in subsequent purification of the acylated ECB compound. Preferably, the tripeptide by-product is removed prior to the reacylation of the ECBN compound.

The tripeptide-aldehyde by-product may be removed from either the fermentation mixture or the mixed broth (i.e., deacylation mixture) by reacting the aldehyde with a derivatizing agent prior to chromatographic purification. The derivatizing agent may be added to the aldehyde functionality to change the chromatographic retention time of the tripeptide-aldehyde in relation to the desired ECB compound. Suitable derivatizing agents include sodium bisulfite, hydroxyl amine and semicarbazide hydrochloride. Some advantages of using derivatizing agents as opposed to other means of modifying the chromatographic retention times are the selectivity of the derivatizing agents for the aldehyde functionality and the mild conditions under which the reaction occurs. If the reaction between the derivatizing agent and the tripeptide-aldehyde is reversible, then the aldehyde can be easily recovered by removing the derivatizing agent. The recovered tripeptide can then be used for other purposes.

EXAMPLES

The following abbreviations are used through out the examples to represent the respective listed materials:

ACN—acetonitrile

TFA—trifluoroacetic acid

HP-20—styrene/divinylbenzene resin having a surface area of 500 m$^2$/g, a pore size of 200–300 Å and particle size of 200–800 μm.

SP-825—styrene/divinylbenzene resin having a surface area of 1,000 m$^2$/g, pore size of 50–60 Å and particle size of 250–600 μm SP-207—brominated styrene/divinylbenzene resin having a surface area of 630 m$^2$/g, pore size of 100–200 Å and particle size of 200–800 μm CG-161CD —styrene/divinylbenzene resin having a surface area of 900 m$^2$/g, pore size of 110–175 Å, and particle size of 80–160 μm.

Chromatographic Preparation and ECBN Purification Procedures

Glass columns were used ranging in size from 0.2 to 5 liters. The chromatographic matrices studied included HP-20, SP-825 and SP-207 (all available form Mitsubishi) and CG-161cd (available from Toso Haas). The matrices were batch washed with 50/50 water/ACN, 0.1 M sodium hydroxide, and finally by pure acetonitrile (ACN) prior to column packing. The matrix of choice was packed into the appropriate size column using simple slurry settling techniques. Column sizes less than one liter were operated using conventional FPLC instrumentation (available from Pharmacia). The five liter column experiments were conducted using a Waters Delta Prep 3000 controller system.

ECBN mixtures were clarified by filtration using Cuno 30S filters prior to loading onto the respective columns. The HP-20 and SP-825 columns were pre-equilibrated in 0.5% acetic acid (HOAc), adjusted to a pH of 5.5 with sodium hydroxide (NaOH), and loaded with the clarified ECBN solution. The HP-20 columns were loaded to approximately 5 to 5.5 g ECBN/liter of packed resin while the SP-825 columns were loaded at approximately 11 to 12 g/liter. After loading, the columns were washed with 5 column volumes (CV) of the equilibration buffer. The product was eluted using a continuous 5 CV, linear gradient ranging from 0.5% HOAc (pH=5.5) to 4% HOAc (pH=2.5). At the end of the gradient, an additional 2 CV of the 4% HOAc solution was used to complete the elution. During elution of the product, 0.2 CV fractions were collected. The fractions were characterized by a variety of reversed-phase HPLC (RP-HPLC) methods, the appropriate fractions were combined to yield the mainstream pool. The columns were regenerated by washing with a 3 CV 60/40 mixture of ACN and water, followed by a 3 CV 60/40 mixture of ACN and 0.1 M NaOH. The flow rates used during the operation were 2 CV/hour (150 cm/hour) for load, wash, regeneration and re-equilibration and 1 CV/hour (75 cm/hour) for elution. The mainstream pools were concentrated.

For comparison, the following mobile phase conditions (organic modifier and pH) and gradient elution profiles were studied in addition to the matrix type.

ACN modifier: Examples 1–3 used a 5 CV, linear ACN gradient (pH 5.5 with an acetate buffer).

Acetic Acid Elution: In addition to the conditions described earlier, the concentration of acetic acid was increased to 5% (Example 10). A step gradient and convex gradient were also compared to the continuous linear gradient described above on both the HP-20 and SP-825 columns (Examples 13–19).

Analytical Characterization of Samples

The quality and quantity of ECBN chromatographic samples were evaluated using the following analytical methods.

Phosphate system: A Zorbox SB C-18, 3.5 micron particle column (0.46 cm ID×15 cm), was eluted with a 0.2% phosphoric acid/ACN mobile phase at a flow rate of 1.0 ml/min. The column was operated at 40° C. and the effluent was monitored at 210 nm. The column is equilibrated in 1% ACN and after sample injection, a gradient ranging from 1 to 18.5% ACN over 9 minutes was used to elute ECBN. After elution, the column was washed with 50% ACN to elute any highly retained components.

Phosphate/Octanesulfonic Acid (OSA) system: This system is similar to the phosphate system discussed above, with the exception that the mobile phase contains 30 mM OSA. The column is equilibrated with 9% ACN. After the sample is injected, elution of ECBN is accomplished with a gradient ranging from 9 to 24% ACN over 9 minutes. The column was then washed with 50% ACN to elute highly retained components. Column flow rate and detector wavelength were as above, while the column temperature was 50° C. This system is particularly useful for quantitating the Asn-Gln-Leu-H tripeptide-aldehyde component.

TFA system: A Vydac C-18, 3.5 micron column (0.46×25 cm) was used for the assay. The mobile phase contained 0.1% TFA and elution was accomplished using a linear ACN gradient of 0 to 10% over 20 minutes, followed by a column wash of 50%. Column flow rate, temperature, and detector wavelength were the same as for the phosphate system described above.

Amino acid analysis (AAA) was also conducted on samples as an alternative method for determining the tripeptide content. Samples were acid hydrolyzed, and the moles of Asn, Gln, and Thr in the hydrolysate were determined by ion exchange chromatography and ninhydrin derivatization. The Thr recovery was used to determine the moles of ECBN in the sample, while the Gln content represented the tripeptide levels. The mole% (M%) of the Asn-Gln-Leu-H tripeptide versus ECBN was calculated using the following equation:

$$M\%\ \text{Asn-Gln-Leu-H} = 2\times(\text{Gln})/(\text{Thr})$$

Optical density (OD) measurements were conducted on select samples at the specified wavelength to estimate relative sample turbidity (OD @550 nm) or total protein content (OD @280 nm).

The following examples are provided to illustrate but not limit the claimed invention.

Example 1

Example 1 compares RP-HPLC chromatographic processes using an acetonitrile elution scheme with an acetic acid elution scheme in combination with a variety of non-functional resins. Table 1 summarizes the results observed using the designated elution schemes and column media.

TABLE 1

| Ex. No. | Matrix type | Column Load[a] | Elution Scheme | ECBN Yield | RP-HPLC purity | % Desmethyl impurity[b] | Mainstream Volume |
|---|---|---|---|---|---|---|---|
| 1* | HP-20 | 3.8 | 0–10% ACN pH 5.5 | 84% | 77.5% | 2.09% | 2.7 |
| 2* | HP-20 | 7.7 | 0–10% ACN pH 5.5 | 66% | 76% | 1.2% | 4.2 |
| 3* | HP-20 | 10.0 | 0–10% ACN pH 5.5 | 48% | 52.3% | 1.2% | 4.2 |
| 4* | HP-20 | 6.0 | 0.5%–4% HOAc step gradient | 82% | 70.5% | 11.4% | 1.8 |
| 5 | HP-20 | 6.0 | 0.5–4% HOAc 7 linear grad. | 69% | 89% | 1.8% | 3.5 |
| 6 | SP-207 | 12.0 | 0.5–4% HOAc 7 linear grad. | 77% | 83% | 6.35% | 3.9 |
| 7 | CG-161 | 6.0 | 0.5–4% HOAc 7 linear grad. | 59% | 90.2% | 1.3% | 3.01 |
| 8 | CG-161 | 10.0 | 0.5–4% HOAc 7 linear grad. | 75.2% | 83% | 2.5% | 4.7 |
| 9* | CG-161 | 8.0 | 100 mM $H_3PO_4$ | 51% | 80% | 3.3% | 4.4 |
| 10 | SP-825 | 12.0 | 0.5–5% HOAc 7 linear grad. | 72% | 78.5% | 5.5% | 2.8 |
| 11 | SP-825 | 14.0 | 0.5–4% HOAc 5 linear grad. | 70% | 82% | 3.57% | 3.0 |
| 12 | SP-825 | 18.0 | 0.5–4% HOAc 5 linear grad. | 83% | 85% | 4.0% | 4.8 |
| 13 | HP-20 | 6.0 | 0.5–4% HOAc 5 linear grad. | 70.5% | 85% | 2.68% | 2.5 |
| 14* | HP-20 | 6.0 | 0.5–4% HOAc Convex 1 CV | 65% | 81.6% | 3.11% | 1.44 |
| 15* | HP-20 | 6.0 | 0.5–4 HOAc Step gradient | 38.5% | 80.4% | 2.93% | 0.77 |
| 16 | SP-825 | 9.1 | 0.5–4% HOAc 5 linear grad. | 77% | 92% | 2.6% | 2.9 |
| 17* | SP-825 | 9.1 | 0.5–4% HOAc Convex grad. | 58% | 91% | 2.5% | 2.7 |
| 18* | SP-825 | 9.1 | 0.5–4% HOAc Step gradient | 56.6% | 89% | 3.4% | 2.3 |
| 19 | SP-825 | 11.8 | 0.5–4% HOAc 5 linear grad. | 59% | 87% | 2.8% | 2.6 |
| 20 | HP-20 | 5.0 | 0.5–4% HOAc 5 linear grad. | 81% | 88% | 2.2% | 2.6 |
| 21 | HP-20 | 6.3 | 0.5–4% HOAc 5 linear grad. | 81% | 86% | 3.3% | 3.0 |

In Table 1,
*Comparative examples;
[a]Measured in grams of ECBN per liter of resin;
[b]Desmethyl impurity refers to a mixture of two ECBN compounds where the methyl group is missing on the threonine and the methyl proline peptide units, respectively.

The (ACN) modifier scheme provided good yield, overall purity and resolution of the desmethyl components; however, acetonitrile is an organic solvent. Table 1 clearly shows that acetic acid provides an alternative to the traditional organic solvent elution scheme. The data also shows that a continuous gradient of acetic acid significantly enhances resolution as compared to either a step gradient or convex gradient of acetic acid. Even though the product yield for Example 5 (linear gradient) is slightly lower and the mainstream volume larger as compared to Example 4 (step gradient), the overall ECBN purity is higher (83% vs. 71%) and the desmethyl content is lower (2% vs. 11%).

The elution of ECBN from the hydrophobic matrix using the acetic acid elution process is believed to be accomplished in two ways: (1) acetic acid acts as an organic modifier, thereby increasing the elution strength of the mobile phase; and (2) the lower pH of the B solvent (strong elution solvent, pH=2.5) serves to protonate the amine functionality of ECBN thus making it more polar and therefore less retained by the hydrophobic stationary phase. Both the organic modifier and pH that affects of the 4% acetic solution are apparent in comparing Examples 8 and 9.

In Example 9, 100 mM phosphoric acid (pH=2.5) was substituted for the 4% HOAc (pH=2.5) as the B solvent. If the elution of the ECBN was dependent only on the pH of the mobile phase, the elution position and recovery of ECBN should be similar to that observed in Example 8. In fact, the phosphate elution resulted in only about 50% recovery of ECBN and the product peak showed a significant degree of tailing. Thus the 4% HOAc may bring about elution by both lowering the pH of the mobile phase and increasing the elution strength of the mobile phase by acting as an organic modifier.

Acetic acid also provides for greater selectivity than acetonitrile. When RP-HPLC chromatograms for mainstreams collected from HP-20 columns eluted with ACN versus HOAc (Examples 1 and 5, respectively) are compared, an absence of backside impurities in the mainstream eluted using HOAc was observed. In the HOAc elution scheme, these components are not eluted until the column is regenerated.

Example 2

Example 2 compares chromatographic processes using a single column/linear acetic acid elution scheme (described above) with a dual column/convex acetonitrile elution scheme. In addition, a comparison between untreated lots of ECBN (Examples 2–8 and 2–10) with ECBN lots treated with sodium metabisulfite prior to purification on the column (Examples 2–7 and 2–9) is described. The pretreatment with sodium metabisulfite was accomplished by simply adding 10 mM of sodium metabisulfite to the column charge and allowing the solution to stir for a period of 6–18 hours. The single column process is the same as described above using a linear gradient acetic acid elution scheme.

The comparative dual column process uses two HP-20 columns that operate in a lead-trail configuration. A fermentation broth is loaded onto two HP-20 columns connected in series. Any ECBN which is not retained by the first column is concentrated on the second column. The ECBN is believed to be distributed in approximately equal proportions between the two columns. After loading, the lead column is disconnected and washed with 3.8 column volumes (CV) of water. Elution of the lead column is accomplished by washing with 3.3 CV of 5% HOAc. The mainstream from the first column is adjusted to a pH of 5.0 and charged onto the partially loaded second (trail) column. The column is washed with 6.3 CV of water prior to elution. A convex acetonitrile gradient (0–9.4% over about 5 CV containing 0.5% HOAc) is used to elute the column. The column effluent is fractionated and fractions having the desired purity (greater than 75% reversed-phase HPLC main peak purity and less than 10% desmethyl component) are pooled as the mainstream. The pooled solution is then concentrated.

Table 2 compares the results observed for the single column versus the dual column chromatographic process, and the treated versus untreated ECBN fermentation broths.

lent to or better than the ECBN purity from the two column process thus providing a more economical means of purification.

None of the column purification schemes were able to significantly reduce the level of the tripeptide; however, pretreatment with sodium bisulfite. significantly reduced the amount of tripeptide impurites. The ECBN/OD purity of the product from the single column studies was equivalent to or greater than that obtained in the two column studies. Although the ECBN/OD value does not represent an absolute measure of purity, it does provide a good relative comparison of the ECBN purity resulting from the various column operations. All of the column operations gave a 10–15 fold increase in ECBN/OD purity when the values for the column charge solutions (data not shown) are compared to those concentrated mainstreams.

All references cited herein, are hereby incorporated herein. Although the foregoing invention has been described in some detail, by way of illustration and example for the purposes of clarity and understanding, it will be apparent to those skilled in the art that certain changes and modifications can be practiced. Therefore, the description and examples should not be construed as limiting the scope of the invention, which is delineated by the appended claims.

What is claimed is:

1. A method for separating and purifying Echinocandin compounds comprising the steps of:
   (i) providing a mixture comprising an Echinocandin compound having attached thereon at least one protonatable amino group;
   (ii) adsorbing said mixture onto a hydrophobic, reversed phase chromatographic media;
   (iii) eluting the Echinocandin compound with a continuous nearly linear acetic acid gradient ranging from

TABLE 2

ECBN Purity Post Column Purification

| Ex. No. | Column type & configuration | Column Load (g/l) | % MP[b] | % Des[c] | % tripeptide | ECBN/OD RO Purity[d] | ECBN Purity Crystal[a] Potency |
|---|---|---|---|---|---|---|---|
| 2-1 | HP-20 | 5.0 | 88.4 | 1.8 | 7.0 | 0.71 | 74.9 |
| 2-2 | SP-825 | 12.0 | 88.2 | 1.9 | 6.2 | 0.59 | 73.1 |
| 2-3 | HP-20/HP-20 |  | 84/7 | 2.2 | 7.1 | 0.53 | 60.5 |
| 2-4 | HP-20 | 5.3 | 83.0 | 2.0 | 11.8 | 0.69 | 76.4 |
| 2-5 | SP-825 | 12.0 | 79.4 | 2.3 | 12.7 | 0.68 | 63.1[e] |
| 2-6 | HP-20/HP-20 |  | 81.9 | 1.7 | 12.8 | 0.67 | 76.8 |
| 2-7 | HP-20 | 4.8 | 87.7 | 1.8 | 1.5 | 0.65 | 74.3 |
| 2-8 | HP-20/HP-20 |  | 84.6 | 1.9 | 7.9 | 0.62 |  |
| 2-9 | SP-825 | 10.5 | 88.2 | 3.2 | 3.3 | 0.56 |  |
| 2-10 | HP-20/HP-20 |  | 79.6 | 2.8 | 13.6 | 0.68 |  |

In Table 2,
[a]Values reported represent the average of two independent crystallizations and analytical determinations;
[b]% Main peak versus total RP-HPLC peak area;
[c]% Desmethyl impurities;
[d]ECBN/OD = grams of ECBN (RP-HPLC)/Total OD grams; where OD grams OD@280 nm and assuming $E_{0.1\%}$ of 1.0;
[e]One of the two lots had high water content; therefore, average potency was reduced.

The analytical results reported above for ECBN purity were obtained after the mainstreams had been concentrated. Both the reversed-phase HPLC main peak purity and the desmethyl levels are similar for the single HP-20 and SP-825 column experiments. However, the single HP-20 operation consistently yields a slightly greater reduction in the desmethyl component. In general, the ECBN reversed-phase HPLC purity of the single column process is equiva- 0.1% acetic acid to 10.0% acetic acid by volume in water; and
(iv) recovering said Echinocandin compound.

2. The method of claim 1 wherein said acetic acid gradient ranges from 0.5% acetic acid to 4.0% acetic acid by volume in water.

3. The method of claim 1 wherein said Echinocandin compound is represented by the following structure:

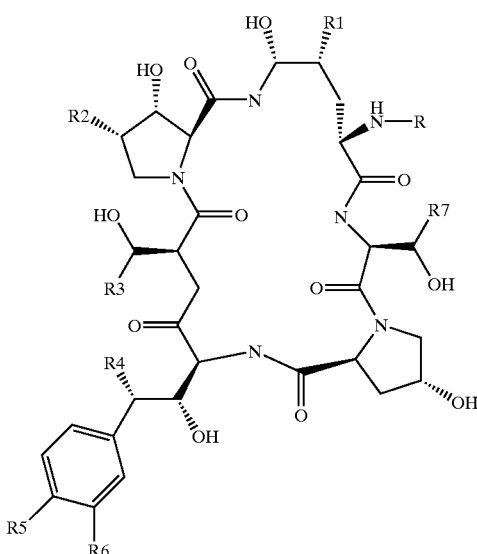

wherein R is a hydrogen or —C(O)R' where R' is an alkyl group, an alkenyl group, an alkynyl group, an aryl group, or heteroaryl group having attached thereon at least one protonatable amino group; R1 is —H or —OH; R2 is —H or —CH$_3$; R3 is —H, —CH$_3$, —CH$_2$CONH$_2$ or —CH$_2$CH$_2$NH$_2$; R4 is —H or —OH; R5 is —OH, —PO$_3$H$_2$, or —OSO$_3$H;—R6 is —H or —OSO$_3$H; and R7 is —CH$_3$.

4. The method of claim 3 wherein R is hydrogen.

5. The method of claim 1 wherein said hydrophobic, reversed-phase media is an organic polymer.

6. The method of claim 5 wherein said organic polymer is a copolymer of styrene and divinylbenzene or a methacrylate polymer.

7. The method of claim 5 wherein said organic polymer is a styrene/divinylbenzene resin having a surface area of 500 m$^2$/g, a pore size of 200–300 Å and particle size of 200–800 μm; or a styrene/divinylbenzene resin having a surface area of 1,000 m$^2$/g, pore size of 50–60 Å and particle size of 250–600 μm.

8. The method of claim 1 wherein said mixture is a product of a mixed broth.

9. A process for purifying Echinocandin compounds from a mixture containing a tripeptide aldehyde by-product comprising the steps of:
(i) providing a mixture of a Echinocandin compound and a tripeptide aldehyde by product;
(ii) adding a derivatizing agent to said mixture to produce a derivatized tripeptide aldehyde product; and
(iii) separating said Echinocandin compound from said derivatized tripeptide aldehyde product using hydrophobic, reversed phase chromatography and eluting with an acetic acid gradient.

10. The process of claim 9 wherein said separating step (iii) comprises:
(a) adsorbing the mixture of derivatized tripeptide aldehyde product and Echinocandin compound onto a hydrophobic, reversed phase chromatographic media; and
(b) eluting the Echinocandin compound with a continuous nearly linear acetic acid gradient ranging from 0.1% acetic acid to 10% acetic acid by volume in water.

11. The method of claim 9 wherein said Echinocandin compound is represented by the following structure:

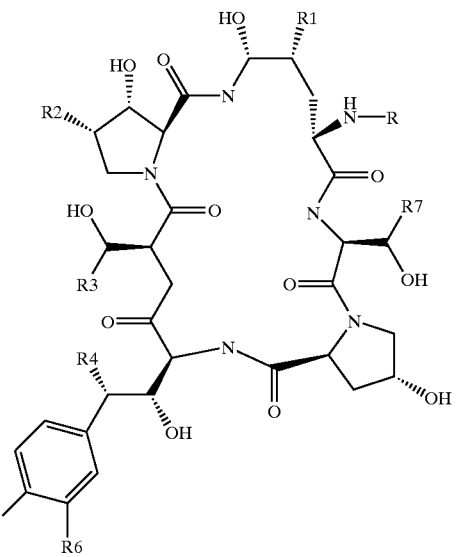

wherein R is a hydrogen or —C(O)R' where R' is an alkyl group, an alkenyl group, an alkynyl group, an aryl group, or heteroaryl group having attached thereon at least one protonatable amino group; R1 is —H or —OH; R2 is —H or —CH$_3$; R3 is —H, —CH$_3$, —CH$_2$CONH$_2$ or —CH$_2$CH$_2$NH$_2$; R4 is —H or —OH; R5 is —OH, —PO$_3$H$_2$, or —OSO$_3$H; R6 is —H or —OSO$_3$H; and R7 is —CH$_3$.

12. The process of claim 11 wherein R is a hydrogen.

13. The process of claim 12 wherein said separating step (iii) comprises:
(a) adsorbing the mixture of derivatized tripeptide aldehyde product and Echinocandin compound onto a hydrophobic, reversed phase chromatographic media; and
(b) eluting the Echinocandin compound with a continuous nearly linear acetic acid gradient ranging from 0.1% acetic acid to 10% acetic acid by volume in water.

14. The process of claim 9 wherein said aldehyde by-product is represented by the following structure:

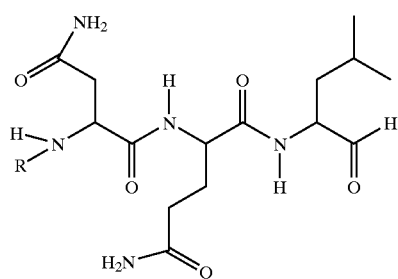

wherein R is —C(O)CH$_2$CH(OH)C$_9$H$_{19}$ or a hydrogen.

15. The process of claim 9 wherein said mixture is a product of a fermentation broth.

16. The process of claim 9 wherein said mixture is a product of a mixed fermentation broth.

17. The process of claim 9 wherein said derivatizing agent is selected from the group consisting of sodium bisulfite, hydroxyl amine and semicarbazide hydrochloride.

18. The process of claim 14 wherein said derivatizing agent is sodium bisulfite.

19. The process of claim 14 wherein said separating step (iii) comprises:

(a) adsorbing the mixture of derivatized tripeptide aldehyde product and Echinocandin compound onto a hydrophobic, reversed phase chromatographic media; and (b) eluting the Echinocandin compound with a continuous nearly linear acetic acid gradient ranging from 0.1% acetic acid to 10% acetic acid by volume in water.

\* \* \* \* \*